United States Patent [19]

Chang et al.

[11] Patent Number: 5,354,881
[45] Date of Patent: Oct. 11, 1994

[54] SILANES CARRYING WATER-SOLUBILIZING AND HYDROPHOBIC MOIETIES

[75] Inventors: Wen-Hsuan Chang, Gibsonia, Pa.; John F. Grunewalder, Nequon, Wis.; Mark A. Harley, Oakmont; Edward E. McEntire, Allison Park, both of Pa.

[73] Assignee: PPG Industries, Inc., Pittsburgh, Pa.

[21] Appl. No.: 776,040

[22] Filed: Oct. 15, 1991

[51] Int. Cl.$^5$ .................... C07F 7/08; C07F 7/10
[52] U.S. Cl. ...................... 556/419; 556/420; 556/423
[58] Field of Search .................. 556/419, 420, 423

[56] References Cited

U.S. PATENT DOCUMENTS

| | | | |
|---|---|---|---|
| 3,922,436 | 11/1975 | Bell et al. | 428/375 |
| 3,956,353 | 5/1976 | Plueddemann | 556/419 |
| 4,822,850 | 4/1989 | Yashuda et al. | 556/420 X |
| 4,822,901 | 4/1989 | Mohr et al. | 556/420 X |
| 4,861,908 | 8/1989 | Satoh et al. | 556/420 |
| 4,997,965 | 3/1991 | Lohmann et al. | 556/420 X |
| 4,997,966 | 3/1991 | Lohmann et al. | 556/420 |

FOREIGN PATENT DOCUMENTS

| | | |
|---|---|---|
| 406731 | 1/1991 | European Pat. Off. . |
| 410264 | 10/1991 | European Pat. Off. . |

OTHER PUBLICATIONS

Chemical Abstract, vol. 99 (1983), No. 217436a (JP 58-95631), Nippon Valqua Ind. Ltd.
Patent Abstract of Japan, vol. 7 (1983), No. 58-167597, Chisso K.K.

*Primary Examiner*—Paul F. Shaver
*Attorney, Agent, or Firm*—Linda Pingitore

[57] ABSTRACT

New organic silanes are claimed carrying at least one water-solubilizing moiety and at least one hydrophobic group suitable for preparing stable solutions or dispersions containing in excess of about five weight percent of such silanes.

18 Claims, No Drawings

SILANES CARRYING WATER-SOLUBILIZING AND HYDROPHOBIC MOIETIES

CROSS REFERENCE TO RELATED U.S. PATENT APPLICATIONS

1. U.S. patent application Ser. No. 07/775,890, filed concurrently herewith, of the same inventors herein for "Stable Aqueous Solutions Containing Siloxanes for Treating Cellulosic substrates" and
2. U.S. patent application Ser. No. 07/776,104 filed concurrently herewith, of Wen Hsuan Chang, Marvin L. Kaufman and Edward E. McEntire, for "Vinyl Polymer Latex Systems".

BACKGROUND OF THE INVENTION

Field Of The Invention

This invention relates to new silanes carrying at least one anionic or nonionic water-solubilizing (hydrophilic) moiety and at least one hydrophobic moiety suitable for preparing stable aqueous solutions or dispersions containing in excess of about five weight percent of said silanes.

Description Of The Prior Art

In Japanese Kokai Patent No. SHO 69(1985)-42437 there is disclosed the reaction of silica with a silane coupling agent carrying an amino group and the subsequent reaction of the product obtained with an anhydride to obtain silica-containing compounds. Pluedemann in U.S. Pat. No. 4,718,944 discloses the reaction product of maleic anhydride and a diamine functional silane compound to obtain an amide-acid product containing silane but devoid of hydrophobic moieties or neutralizing moieties. Holub et al in U.S. Pat. No. 3,755,354 are interested in imido-substituted organosilanes and an intermediate amide acid devoid of neutralizing moieties. None of these references relates to new silanes carrying at least one neutralized anionic or nonionic water-solubilizing moiety and at least one hydrophobic moiety suitable for the preparation of stable aqueous solutions or dispersions containing in excess of about five weight percent of said novel silanes.

SUMMARY OF THE INVENTION

The aqueous dispersion of the novel silanes claimed herein contain in excess of about 5 weight percent of the silanes. The novel silanes carry at least one anionic or nonionic water-solubilizing moiety and at least one hydrophobic moiety and can be defined by the following structural formula:

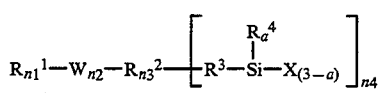
(I)

wherein $R^1$ represents a monovalent organic moiety having from 6 to 30 carbon atoms, preferably from 7 to 20 carbon atoms, such as aryl, alkaryl or aralkyl radicals, optionally containing one or more heteroatoms, such as O, N or S and functional groups, such as OH, $CO_2$, ethers, amines, amides or carbon-to-carbon double bonds;

$R^2$ represents a divalent organic moiety, such as alkylidene, cycloalkylidene, arylidene, alkarylidene or aralkylidene radicals, optionally containing one or more heteroatoms, such as O, N or S, and functional groups, such as OH, $CO_2$, ethers, amines, amides or carbon-to-carbon double bonds, provided that the total number of carbon atoms in $R^1 + R^2$ is at least 5, preferably at least 7, most preferably 7 to 26;

$R^3$ represents a divalent organic radical having a carbon directly attached to silicon having from 2 to 30 carbon atoms, preferably from 2 to 6 carbon atoms, such as ethylidene, propylidene, hexylidene or phenylene, which can contain one or more heteroatoms, such as O, N or and functional groups such as OH, $CO_2$, ethers, amines, amides or carbon-to-carbon double bonds;

$R^4$ represents radicals selected from the group consisting of H and a lower alkyl, preferably $CH_3$;

W represents a moiety selected from the group consisting of AZ and $O(CH_2CHR^5O)_m$; wherein $R^5$ represents H or a lower alkyl, such as $CH_3$, preferably H, with the proviso that when W is AZ, $n_1$ is 0 and when W is $O(CH_2CHR^5O)_m$, $n_1$ is 1;

A represents a radical selected from the group consisting of $CO_2$ and $SO_3$;

Z represents a radical selected from the group consisting of $NR^6R^7R^8R^9$ and an alkali metal, such as Na and K, preferably Na; wherein $R^6$ represents H or a lower alkyl, such as $CH_3$ and $R^7$, $R^8$ and $R^9$ represent, independently, radicals selected from the group consisting of H, lower alkyls having from 1 to 3 carbon atoms, preferably methyl and ethyl, wherein the above-mentioned alkyl groups can contain hydroxy groups, provided that in combination the formula weight of $R^7$, $R^8$ and $R^9$ totals less than about 300, preferably less than about 200;

X represents a halide, such as Cl or Br, preferably Cl, or the radical $OR^{10}$, but preferably the radical $OR^{10}$;

$R^{10}$ represents H, a lower alkyl having from 1 to 3 carbon atoms, preferably methyl and ethyl, an aryl or alkaryl organic group having 6 to 10 carbon atoms or

$R^{11}$ represents a lower alkyl having from 1 to 2 carbon atoms, preferably methyl;

$n_1$ is the integer 0 or 1;

$n_2$ is the integer 1 to 3, preferably 1 or 2;

$n_3$ is the integer 0 or 1;

$n_4$ is the integer 1 to 2, preferably 1;

$n_5$ is the integer 0 or 1, preferably 0;

a is the integer 0 or 1, preferably 0; and m is the integer ranging from 5 to about 70, preferably from about 10 to about 55.

The preferred novel silanes claimed herein having at least one water-soluble moiety and at least one hydrophobic moiety can be defined by the following structural formulas:

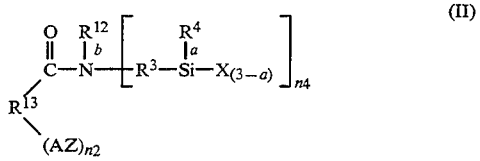

(II)

wherein
R$^{12}$ represents H, an alkyl radical having from 1 to 20 carbon atoms, a cycloalkyl radical having from 6 to 10 carbon atoms, an aryl radical having from 6 to 10 carbon atoms, or an alkaryl radical having from 7 to 20 carbon atoms, said radicals optionally containing one or more heteroatoms, such as O, N or S, and functional groups, such as OH, CO$_2$, ethers, amines, amides or carbon-to-carbon double bonds;
R$^{13}$ represents a divalent organic moiety, such as alkylidene, cycloalkylidene, arylidene, alkarylidene or aralkylidene radicals, optionally containing one or more heteroatoms, such as O, N or S, and functional groups, such as OH, CO$_2$, ethers, amines, amides, or carbon-to-carbon double bonds, provided that the total number of carbon atoms in R$^{12}$ and R$^{13}$ is less than 30, preferably less than about 25;
b is the integer 0 or 1;
A, Z, R$^3$, R$^4$, a, n$_2$ and n$_4$ are defined as above; and

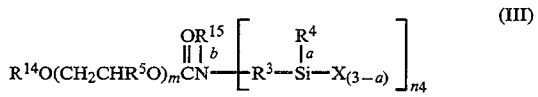

(III)

wherein
R$^{14}$ represents a hydrophobic monovalent aryl, alkaryl or aralkyl organic radicals having from 6 to 26 carbon atoms, preferably 7 to 20 carbon atoms, said radicals optionally containing a functional group, such as ether, amide or ester;
R$^{15}$ represents H or a lower alkyl, such as CH$_3$; and
R$^3$, R$^4$, R$^5$, X, a, b and n$_4$ are as defined above.

We believe that each of the compounds defined above will always have an HLB [hydrophilic(water-soluble moieties)-lipophilic(hydrophobic moieties) balance] of at least 10 when the same are dissolved in water, as determined by the method described in Kirk-Othmer, Encyclopedia of Chemical Technology, Third Edition, Volume 8, John Wiley & Sons, New York, N.Y. (1979), starting on page 910. HLB is an expression of the relative simultaneous attraction of a compound, for example, an emulsifier, for water and oil (or for the two-phases of the emulsion system being considered). This 10+ HLB requirement will serve to further define the nonionic hydrophilic moiety in relation to the hydrophobic moiety.

In the above, by "hydrophobic moiety", we mean to include those moieties which are capable of repelling water and encourage micelle formation. By "water-solubilizing moiety" we mean to include those moieties which are polar organic or inorganic groups. Examples of these are neutralized acid groups, such as carboxylic acid or sulfonic acid salts, and polyoxyethylene moieties. By "polyoxyethylene moieties", we mean predominantly polyoxyethylene units in the polymer chain which may have interspersed within small amounts of polyoxypropylene units, said amounts of polyoxypropylene units consisting of about 20 percent by weight or less of the total polyoxyethylene-polyoxypropylene polymer chain. By "solution" we mean a clear aqueous liquid, for example, water, having dissolved therein one or more compounds, for example, those defined above. By "dispersion", we mean a cloudy or whitened liquid under visible light. The aqueous system usually contains a solid or a liquid having a particle size in the range of about 10 to about 200 nanometers uniformly dispersed in a carrier liquid, such as water.

Silanes containing silicon carrying two or more hydrolyzable groups for many years were believed to be unstable in the presence of excess water when the silane was added thereto in high concentrations, that is, in concentrations from about five to 60 weight percent, or even higher. Only some silanes with special structural features, i.e., aminopropylsilanes were known in some restricted situations to form stable solutions, or unstable compositions depending on the experimental conditions, but these had neither hydrophobic moieties or water-solubilizing moieties. Thus, many low molecular weight silanes have been commercially employed at high dilution (less than about five weight percent in water). Thus, they are often used for treating inorganic fibers as adhesion promoters to chemically bind these fibers to an organic polymer, plastic or resin, as described, for example, in U.S. Pat. No. 3,973,057, referred to above. We have found that we can introduce our novel silanes in water in amounts in excess of about five weight percent, in fact as high as about 60 weight percent, and still have a composition that retains its stability over longer periods of time, for example, up to about 100 days, or even longer. By "stability" we mean that the aqueous mixture containing the silane will not gel or coagulate. This stability is highly desired because it permits shipment of these products with a minimum freight expense, because of the higher concentration of silane therein, and also permits storage over a long period of time. These aqueous products are, of course, not moisture sensitive as are organosilanes of the prior art. The non-aqueous silanes of the prior art when exposed to atmospheric moisture react with water to form condensates which lead to insoluble material, which can subsequently plug applicator devices (such as spray guns) or result in skinning over in an open container containing the same. The aqueous solutions prepared using the novel silanes herein do not suffer from these application disadvantages. Because of the combination of the unusual properties the aqueous solutions or dispersions prepared using the novel silanes claimed herein require no organic solvent for viscosity reduction after addition to water and therefore are more environmentally desirable than solvent-borne silanes of the prior art. When the aqueous solutions are used to treat wood or similar products it is surprising to find our materials stabilize the same against weathering (bleaching, darkening, discoloring, degrading of fibers or lignin, photodegradation, etc.).

The novel silane compounds claimed herein are easily obtained. To obtain the artionic-containing compounds of Group (I) above, reactants that are useful include organic anhydrides and aminosilanes which contain either mono- or di-substituted amines as follows:

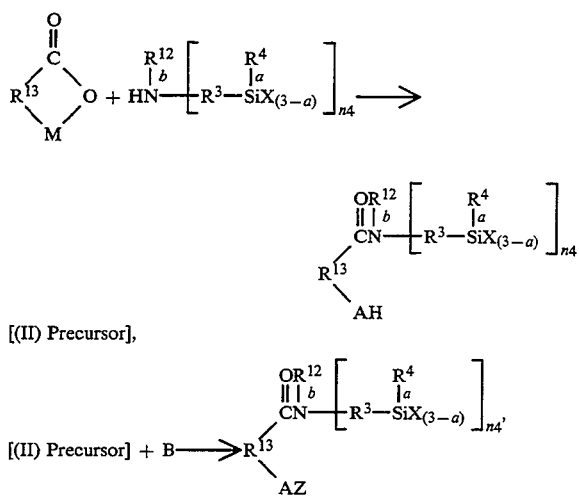

[(II) Precursor],

[(II) Precursor] + B ⟶ wherein each of the parameters above are as previously defined, except M and B, and M is C=O or SO₂ and B is a base, such as ammonia, an amine, such as triethylamine, N,N-dimethylethanolamine, ethanol amine, tetraethylammonium hydroxide, sodium hydroxide, sodium methoxide and potassium t-butoxide.

The order of addition of aminosilane and anhydride is not important and when the base B is added is important only when the base is reactive with the anhydride. For example, the addition of a non-tertiary amine base, such as ammonia, (one mole) to the anhydride (one mole) may produce a reaction resulting in the destruction of the anhydride functionality, which would then be unavailable for reaction triethylamine, would not react with the anhydride, and therefore could be mixed with the anhydride prior to addition of the aminosilane. One skilled in the art will know the proper methods of mixing the reagents to produce the instant, desired compound.

The reaction between the organic anhydride and the amine silane is often spontaneous and requires no heating, but heat may be applied to speed the reaction. Typically, one reactant is added slowly to the other with stirring to avoid a significant exotherm which may cause formation of cyclic imide (when R¹² is H) as discussed by Holub et al in U.S. Pat. No. 3,755,354, referred to above. The reaction temperature should generally be kept below about 100° C. to inhibit formation of significant amounts of imide, although the presence of imide is not harmful to useful wood stabilizing properties, wherein the compounds defined herein find significant applications. When the imide to amide-acid ratio starts to exceed certain ratios (for example, about 2:1) the compounds may become unstable and insoluble when introduced into water, since insufficient water-solubilizing groups may be present to solubilize both the amide acid and the imide (which has no water-solubilizing group).

The reaction of the base B with the amide-acid intermediate can be accomplished by adding the base to the a/Bide-acid. The neutralization is generally exothermic. Alternatively, the amide-acid can be added to water containing the base, thus instantly forming the composition of this invention.

The selection of base B may influence the stability of the composition when added to excess water. Trial and error method must be used to obtain a stable product. It is not uncommon that a composition neutralized with triethylamine can have excellent stability when added to water, but the same composition when neutralized with ammonia at the same weight percent solids could provide a less stable dispersion in water. In such cases, more water may be used to obtain stable compositions. Preferred amines are generally triethylamine and N,N-dimethylethanolamine.

The mole ratio of aminosilane to anhydride can vary. The exact stoichiometry is not critical, and the mole ratio can be from about 0.5:1 to about 1:0.5, preferably from about 0.8:1 to about 1 to about 0.8. The amount of silicon present in the claimed compound is important when the compound is used in treating wood. The amount required for good performance can range from about 0.1 to about 12 weight percent, preferably from about 1.0 to about 8 weight percent. When R³ or R¹² of [(II) Precursor] contains a reactive heteroatom group, such as —NH—, additional anhydride in excess of one mole can be added to react with the second amine in the aminosilane. The excess anhydride need not be the same as the one originally used.

The reaction is typically carried out in the absence of a solvent, but any water-compatible and unreactive solvent, such as a polar aprotic solvent, for example, ethyl acetate or tetrahydrofuran can be used for viscosity reduction. Tertiary non-hydroxylic amines, such as triethylamine, can be used both as a reaction solvent and neutralizing agent. Solvents can be removed or retained following the described reaction. Thus, gamma-aminopropyltrimethoxy silane can be reacted with octenylsuccinic anhydride to give a mixture containing the necessary moieties—carboxylic acid moiety (anionic moiety), octenyl moiety (hydrophobic moiety) and silane containing methoxy groups (hydrolyzable moiety). The composition will also contain the additional moieties—amide, carbon-to-carbon double bond and may contain imide. Gamma-aminopropyldiethoxysilane and methylhexahydro phthalic anhydride will result in a composition having the same necessary moieties as above. The ethoxy groups on the Si are hydrolyzable. Similarly 2-sulfobenzoic acid cyclic anhydride and gamma-aminopropyltriethoxysilane result in a mixture containing sulfonic acid moiety (anionic moiety), benzilidene moiety (hydrophobic moiety) and an additional amide moiety. The ethoxy groups on the silicon are hydrolyzable.

The nonionic compounds (III) when R¹⁵ is H, can be prepared by reacting an isocyanate terminated silane of the following structure:

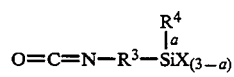

wherein each parameter is as defined above, with a hydroxyl-containing, non-ionic surfactant having an HLB of about 10 or more up to about 20. Typically, urethane catalysts of tertiary amines, such as 1,4-diazobicyclo [2,2,2]octane or tin compounds, such as dibutyltin dilaurate or stannous octoate, can be used to lower the reaction time or temperature. These catalysts are useful in amounts ranging from about 0.01 to about 1 by weight of isocyanate. The reaction temperature can vary widely, but practically will range from about ambient temperature to about 100° C. The reaction time typically will be from about 30 minutes to about 10 hours. Pressure is typically ambient. A polar or nonpolar, non-hydroxylic solvent can be used, but generally is not needed. Thus, the ethoxylate of nonylphenol containing 40 moles of ethylene oxide can be reacted with gamma-isocyanato propyltriethoxysilane to yield a composition containing a polyethylene oxide, water-solubilizing moiety, and a nonylphenyl hydrophobic moiety, along with the alkoxysilane moiety which has ethoxy groups that are hydrolyzable. An additional moiety present is urethane. No ionic groups are present.

DESCRIPTION OF PREFERRED EMBODIMENTS

Example 1

A. To a two-liter flask equipped with a nitrogen sparger an addition funnel and stirrer, there was charged 747 grams of dodecenylsuccinic anhydride. Then 452.8 grams of gamma-aminopropyltrimethoxysilane was added dropwise with stirring over a period of 1.8 hours. The temperature of the mixture reached 60° C. during the addition. Following the subsidence of the exotherm, the acid number was 128, and the amine equivalent weight was 6160. No anhydride was detected by infrared analysis and C=O absorbtions were present at 1635 and 1705 cm$^{-1}$, indicating the presence of amide and acid groups. To 320.2 grams of the above product was added 74.0 grams of triethylamine. The density of the product was found to be 8,224 pounds per gallon and the solids content 73.0 weight percent. This product (350 grams), containing a hydrophobic dodecenyl moiety and an anionic water-solubilizing moiety (an amine salt of a carboxylic acid) was added to 284.3 grams of water to produce a clear aqueous solution containing 45 weight percent of the new product claimed herein, which hydrolyzed to a solution of 40.2 weight percent of calculated solids having Si—O—Si bonding.

B. In a glass reactor, 1 mole of dodecenylsuccinic anhydride and 1 mole of gamma-aminopropyltrimethoxysilane were mixed and allowed to exotherm. The temperature reached approximately 90° C. The resulting acid was neutralized with triethylamine (1 eg. per 1 eg. acid). The product was poured into water to give a 45% solution in water. The Gardner-Holdt viscosity was Y—, the acid value was 48.3.

Example 2

116.85 grams of isooctadecenylsuccinic anhydride and 59.77 grams of gamma-aminopropyltrimethoxysilane were combined in a reactor with stirring and allowed to exotherm. When the mixture reached ambient temperature, 33.73 grams of triethylamine was added thereto. The resulting product had a Gardner-Holdt viscosity of V+, a Gardner color of 3–4 and an acid value of 50.6, consistent with an acid group being present. An infrared spectrum of the product showed no remaining anhydride. The product obtained was an amine-neutralized amide-acid silane with hydrolyzable methoxy groups. Some cyclic imide was likely also present. The isooctadecenyl group serves as the hydrophobic moiety, and the neutralized acid serves as the water-solubilizing group.

Example 3

To a nitrogen padded flask there was charged 291.8 grams of methylhexa hydrophthalic anhydride and then 308.2 grams of gamma-aminopropyltrimethoxy silane was added dropwise over a period of about four hours. The maximum temperature of the exotherm was 66° C. The final acid number was 130.6, and the amine equivalent 2308. An infra-red spectrum showed no remaining anhydride. The acid generated from the reaction was neutralized with triethylamine. The product obtained was an amine-neutralized amide-acid silane. The methylcyclohexylidene moiety serves as the hydrophobic moiety and the amine-neutralized acid serves as the water-solubilizing group.

Example 4

To a 250 milliliter flask there was added 121 grams (0.05 mole) of Igepal CO 970 [nonylphenoxypoly(ethyleneoxy) ethanol, obtainable from GAF Corporation] and the contents thereof were warmed with nitrogen to 55° C.

Then 12.35 grams of isocyanatopropyltriethoxysilane was added with stirring. Following this, 0.133 gram of dibutyltin dilaurate catalyst was added, and the mixture was heated to 90°–95° C. and held at this temperature level for about two hours. No isocyanate was present by infra-red analysis. The product was a waxy solid after cooling to ambient temperature. The compound obtained was a urethane-silane containing a water-solubilizing poly(oxyethylene) group. The nonyl phenyl group serves as the hydrophobic moiety.

To 26.3 grams of the above compound there was added 26.3 grams of water, and the mixture was stirred and warmed to dissolve the compound. The following dilutions were made:

TABLE I

| Grams of Above Mixture | Grams of Water | Weight Percent Solids |
|---|---|---|
| 10.0 | 2.25 | 40 |
| 5.0 | 5.0 | 25 |
| 5.13 | 11.97 | 15 |
| 5.0 | 50 | 5 |

Each of these solutions was found to be stable, in that no change in physical condition of the solutions occurred, on storage at 120° F. for 27 days.

Example 5

To a glass reactor with a nitrogen atmosphere 62.4 grams of benzylamine was charged and heated to 50° C. Then 137.6 grams of glycldoxypropyl trimethylsilane was added dropwise over a period of two hours. Heating was continued at 50° C. for three hours, when the temperature was raised to 80° C. After one hour at 80° to 85° C., the epoxy equivalent weight was 4031. To 195 grams of the above product at 30° C. there was added 121.9 grams of octenylsuccinic anhydride dropwise over 1.6 hours. The reaction was exothermic and the temperature increased to 40° C. When the temperature dropped to 35° C., the contents were heated to 60° to 65° C. for one hour. Then 20.6 grams of isopropanol was added to reduce the viscosity, and the product was cooled. The acid number was 96.0, the infrared spectrum showed no anhydride remaining and the amine equivalent weight was 1378.

Twenty grams of the above solution was added to a stirred mixture of 3.46 grams of triethylamine and 23.5 grams of deionized water. A clear solution resulted, which was 40 weight percent solids and 100 percent neutralized.

A similar solution to that above passed a hot storage accelerated stability test of 120° F. for three days with no apparent change. A similar dispersion with ammonia as neutralizing agent instead of triethylamine at 10 weight percent solids, instead of 40 weight percent solids, was still very fluid, but had some sediment in the bottom of the sealed jar after three days at 125° F. Therefore, the triethylamine neutralizer performs better yielding a more stable product than ammonia in this comparison.

EXAMPLE 6

To 382 grams of bis(trimethoxysilylpropyl)amine was added portion-wise over 1.5 hours to 148 grams of phthalic anhydride at between 24° and 70° C. Some heat was applied to begin the exothermic reaction at the early stages. The reaction rate and the temperature of 55° to 70° C. were then maintained by adding the phthalic anhydride, with only slight heating required. The product was then cooled, after which 33.2 grams of isopropanol was added to reduce viscosity. The product had an acid number of 102.9 and an amine equivalent weight of 17. No anhydride was present by infrared analysis.

The reaction product was dispersed into 23.3 grams of water and 3.71 grams of triethylamine to form a hazy dispersion (40 weight percent solids and 100 percent neutralized), which gelled in about two minutes. A dispersion using ammonia in place of triethylamine gave a poorer dispersion, which also gelled. Even at 10 weight percent solids the dispersion was poor. This shows that an aminodisilane carrying a six carbon hydrophobic group will not give a stable aqueous solution.

Example 7

To 223 grams of N(beta-aminoethyl)-gamma-aminopropyltrimethoxysilane in a flask equipped with a stirrer and nitrogen atmosphere there was added dropwise over four hours 196 grams of a 50 weight percent solution of maleic anhydride in ethyl acetate. During the addition, 138.2 grams of ethyl acetate was added to reduce viscosity. The maximum temperature was 43° C. Then 253 grams of dodecenyl succinic anhydride was added dropwise over 1.5 hours. After 0.5 hour more, anhydride was still present, and the amine content was 0.69 meq/gram. The reaction mixture was heated to 50° to 55° C. and held for 4.75 hours. No anhydride remained, and the residual amine content was 0.34 meq/gram. The acid value was 137.

100.64 grams of the above composition was mixed with 21.1 grams of triethylamine (84 percent neutralization) which reacted exothermically to provide the amine-acid salt. Then 93.4 grams of water was added and the mixture again exothermed when the sample was mixed, again to about 45° C. maximum. The product was theoretically 38.8 weight percent solid (actual 37.4 weight percent solids measured by evaporating about one gram for one hour at 110° C.). The Gardner-Holdt viscosity was A when measured the following day.

Example 8

A two-liter reactor equipped with a stirrer, reflux condensor, thermocouple and nitrogen atmosphere was charged with 223 grams of N(beta-aminoethyl)-gamma-aminopropyl-trimethoxy silane. By means of an addition funnel, 443 grams of dodecenyl succinic arthydride was added dropwise with stirring over 5.75 hours. The exotherm produced a maximum temperature of 46° C. During the addition, after about one-third of the addition, 91 grams of dry ethylacetate was added to reduce the increasing viscosity. At about half way through the addition, 158 grams of additional ethyl acetate was added. Thirty minutes after the addition was complete, the amine content was 0.7 meq/gram and a small amount of anhydride remained as observed from an infrared spectrum. After heating to 50° C. for 1.25 hours, no anhydride remained, the amine content was 0.65 meq/gram. The acid value was 91.0.

106.0 grams of the above product and 20.9 grams of triethylamine (89 percent neutralization) were mixed. Then 93.0 grams of water was mixed in. The maximum temperature of mixing was 40° C. The next day following mixing the product, a clear brown solution, had a Gardner-Holdt viscosity of B, and an analyzed solids content of 32.1 weight percent (110° C./one hour).

Example 9

To a nitrogen blanketed reactor containing 23.4 grams of gamma-aminopropyltrimethoxysilane and 13.2 grams of triethylamine there was added portionwise with stirring 9.32 grams of ortho-sulfobenzoic anhydride. The mixture was reacting slowly as evidence by a mild exotherm. Then 39.9 grams of acetonitrile was added to eliminate the heterophase mixture. However, a slurry remained. Portion-wise additions of sulfobenzoic arthydride continued with exotherm as high as 55° C. until a total of 27.4 grams of sulfobenzoic anhydride had been added over about 1.5 hours total. The acid value of the resulting slurry was 104.2. The amine content by HCl titration was 0.85 meq/gram.

To 19.1 grams of deionized water was added with stirring 29.66 grams of the above solution. A clear solution resulted which was orange-brown. The solution had a pH of 8.25 and a measured solids content (by evaporation of about one gram sample at 110° C. for one hour) of 31.2 weight percent solids.

Example 10

A stain containing a siloxane wood preservative of this invention was prepared by stirring together the following ingredients:
15.0 grams of the product of Example 1B above,
90.4 grams of deionized water,
0.35 grams of a defoaming surfactant[1], and
4.0 grams of the tint paste described below.

Tint Paste

A tint paste was prepared by grinding together the following:
8 pints by weight of carbon black,
270 parts by weight of yellow iron oxide,
50 parts by weight of red iron oxide,
185 parts by weight of deionized water,
7.4 parts by weight of defoaming surfactant[1],
1.4 parts by weight of Tinuvin 1130[2] light stabilizer.
200 parts by weight of water based acrylic grind resin[3].

[1]Surfynol 104, an acetylenic diol, available from Air Products.
[2]Available from Ciba-Giegy.
[3]A 39 weight percent aqueous solution of an acrylic polymer containing about 12 weight percent acrylic acid.

Pine blocks (4"×12"×1") and luan blocks (6"×12"×1") were dipped into a preservative treatment similar to that used in U.S. Pat. No. 4,404,239, Example 2, for about 30 seconds. The blocks, following draining and drying overnight, were then sprayed on one side with (1) the siloxane-preservative stain prepared above, (2) with a silane solvent and based stain of U.S. Pat. No. 4,913,972, Example 8b, or (3) with no silicon composition and only stain for comparison. The above sprays produced a wet film thickness of about 4 mils, which rapidly soaked into the wood.

After standing at ambient temperature overnight, topcoats were applied as follows (to the face of the board treated with the stains above):

Solutions of polyurethane precursors similar to those used in Example 3 of U.S. Pat. No. 4,913,972 were prepared at 40 weight percent solids and at 56 weight percent solids. Solvents used for the dilutions were methyl amylketone, xylene, and oxyhexyl acetate. The first coat at 40 weight percent solids was sprayed at 1.5-2 mils wet film thickness, which was flashed 10 minutes at ambient temperature and followed by spraying the 56 weight percent solution of the same polyurethane composition. The boards were then flashed 10 minutes at ambient temperature, followed by baking at 120° F. for 20 minutes to cure the urethane formulation. Thus two types of wood were treated identically with and without siloxane or silane preservatives. Two boards of each type were treated and placed on exposure.

After 2 years in Florida, South 45° exposure, of the above pine and luan boards with control boards comparing no silane or siloxane treatment, the following results were observed:

| Board Number | |
| --- | --- |
| Pine board, controls, no silane or siloxane) | |
| one | no failure, film integrity good |
| two | crack in board and coating |
| Pine board, with siloxane of this invention | |
| one | no failure, good film performance |
| two | no failure, good film performance |
| Pine board, with silane of U.S. Pat. No. 4,913,972 | |
| one | no failure, good film performance |
| two | no failure, good film performance |
| Luan, control (no siloxane or silane) | |
| one | discontinued test due to mildew spotting |
| two | discontinued test due to mildew spotting |
| Luan, with siloxane of this invention | |
| one | no failure, good film performance |
| two | no failure, good film performance |
| Luan, with silane of U.S. Pat. No. 4,913,972 | |
| one | discontinued test due to mildew spotting |
| two | discontinued test due to mildew spotting |

Good film integrity was observed for the products of this invention, and no film failures were recorded. In this test with luan, the siloxane treated boards outlasted even the boards treated with the silanes of U.S. Pat. No. 4,913,972.

Obviously, many modifications and variations of the invention, as hereinabove set forth, can be made without departing from the spirit and scope thereof, and therefore only such limitations should be imposed as are indicated in the appended claims.

We claim:

1. Aqueous dispersions of novel silanes containing in excess of about 5 weight percent of the silanes, said novel silanes carrying at least one anionic or nonionic water-solubilizing moiety and at least one hydrophobic moiety having the following structural formula:

$$R^1_{n_1}-W_{n_2}-R^2_{n_3}-\left[R^3-Si-X_{(3-a)}\right]_{n_4}^{R^4_a} \quad (I)$$

where $R^1$ represents a monovalent organic moiety selected from the group consisting of aryl, alkaryl and aralkyl radicals having from 6 to 30 carbon atoms and which may contain one or more heteratoms selected from the group consisting of O, N and S and functional groups selected from the group consisting of OH, $CO_2$, ethers, amines, amides and carbon-to-carbon double bonds;

$R^2$ represents a divalent

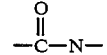

containing organic moiety selected from the group consisting of alkylidene, cycloalkylidene, arylidene, alkarylidene, and aralkylidene, with the total number of carbon atoms in $R^1+R^2$ being at least 5 and which may contain one or more heteratoms selected from the group consisting of O, N and S and functional groups selected from the group consisting of OH, $CO_2$, ethers, amines, amides and carbon-to-carbon double bonds;

$R^3$ represents a divalent organic radical having a carbon directly attached to silicon and which may contain one or more heteratoms selected from the group consisting of O, N and S and functional groups selected from the group consisting of OH, $CO_2$, ethers, amines, amides and carbon-to-carbon double bonds;

$R^4$ represents radicals selected from the group consisting of H and a lower alkyl;

W represents a moiety selected from the group consisting of AZ and $O(CH_2CHR^5O)_m$, wherein $R^5$ represents H or a lower alkyl; with the proviso that when W is AZ, $n_1$ is 0; and when W is $O(CH_2CHR^5O)_m$, $n_1$ is 1;

A represents a radical selected from the group consisting of $CO_2$ and $SO_3$;

Z represents a radical selected from the group consisting of $NR^6R^7R^8R^9$ and an alkali metal, wherein $R^6$ represents H or a lower alkyl and $R^7$, $R^8$ and $R^9$ independently represent radicals selected from the group consisting of H and a lower alkyl, with the formula weight of $R^7+R^8+R^9$ being less than about 300;

X represents a halide, or the radical $OR^{10}$, wherein $R^{10}$ represents H, a lower alkyl, aryl or alkaryl organic radicals or

wherein $R^{11}$ represents a lower alkyl;

$n_1$ is the integer 0 when W is AZ; $n_1$ is the integer 1 when W is $O(CH_2CHR^5O)_m$;

$n_2$ is the integer 1 or 3;

$n_3$ is the integer 1;

$n_4$ is the integer 1;

$n_5$ is the integer 0 or 1;

a is the integer 0 or 1; and m is the integer ranging from 5 to 70.

2. The aqueous dispersions of claim 1 wherein at least one of $R^1$ and $R^3$ contains at least one heteroatom and at least one functional group.

3. The aqueous dispersions of claim 1 wherein $R^2$ additionally contains at least one further heteroatom and at least one further functional group.

4. The aqueous dispersions of claim 1 wherein the total number of carbon atoms in $R^1+R^2$ is at least 7.

5. The aqueous dispersions of claim 4 wherein the total number of carbon atoms in $R^1+R^2$ is from 7 to 26.

6. The aqueous dispersions of claim 1 wherein W represents the moiety AZ and $n_1$ is 0.

7. The aqueous dispersions of claim 1 wherein W represents the moiety $O(CH_2CHR^5O)_m$ and $n_1$ is 1.

8. The aqueous dispersions of claim 6 wherein Z represents the radical $NR^6R^7R^8R^9$.

9. The aqueous dispersions of claim 6 wherein Z represents an alkali metal.

10. The aqueous dispersions of claim 6 wherein A represents a radical selected from the group $CO_2$ and $SO_3$.

11. The aqueous dispersions of claim 1 wherein X represents $OR^{10}$.

12. Novel silanes carrying at least one artionic or nonionic water-solubilizing moiety and at least one hydrophobic moiety having the following structural formulas:

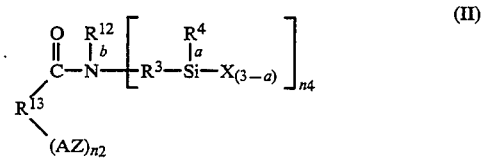

wherein
$R^{12}$ represents H, an alkyl, cycloalkyl, aryl or an alkaryl radical and may contain one or more heteratoms selected from the group consisting of O, N and S and functional groups selected from the group consisting of OH, $CO_2$, ethers, amines, amides and carbon-to-carbon double bonds;

$R^{13}$ represents a divalent organic moiety selected from the group consisting of alkylidene, cycloalkylidene, arylidene, alkarylidene, and aralkylidene, with the total number of carbon atoms in $R^{12}+R^{13}$ being at least 5 and less than about 30 and which may contain one or more heteratoms selected from the group consisting of O, N and S and functional groups selected from the group consisting of OH, $CO_2$, ethers, amines, amides and carbon-to-carbon double bonds;

$R^3$ represents a divalent organic radical having a carbon directly attached to a silicon;

$R^4$ represents radicals selected from the group consisting of H and a lower alkyl;

A represents a radical selected from the group consisting of $CO_2$ and $SO_3$;

Z represents a radical selected from the group consisting of $NR^6R^7R^8R^9$ and an alkali metal, wherein $R^6$ represents H or a lower alkyl and $R^7$, $R^8$, and $R^9$ independently represent radicals selected from the group consisting of H and a lower alkyl, with the formula weight of $R^7+R^8+R^9$ being less than about 300;

X represents a halide or the radical $OR^{10}$, wherein $R^{10}$ represents H, a lower alkyl, aryl or alkaryl radicals or

wherein
$R^{11}$ represents a lower alkyl;
$n_2$ is the integer 1 to 3;
$n_4$ is the integer 1;
a is the integer 0 or 1;
b is the integer 1; and

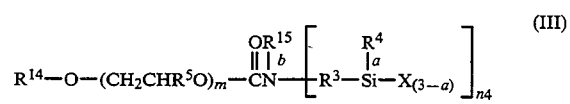

wherein
$R^{14}$ represents a hydrophobic monovalent aryl, alkaryl or aralkyl organic radical;
$R^5$ represents H or a lower alkyl;
$R^{15}$ represents H or a lower alkyl;
$R^3$ represents a divalent organic radical having a carbon directly attached to silicon;
$R^4$ represents radicals selected from the group consisting of H and a lower alkyl;
X represents a halide, or the radical $OR^{10}$, wherein $R^{10}$ represents H, a lower alkyl, aryl or alkaryl organic radicals or

wherein
$R^{11}$ represents a lower alkyl;
m is an integer ranging from 5 to 70;
a is the integer 0 or 1;
b is the integer 1; and
$n_4$ is the integer 1.

13. The silanes of claim 12 wherein said silanes are defined by the following structural formula

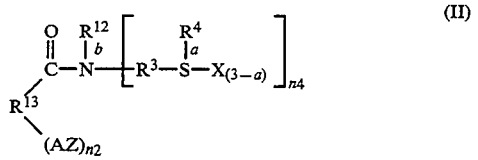

wherein
$R^{12}$ represents H, an alkyl, cycloalkyl, aryl or an alkaryl radical;
$R^{13}$ represents a divalent organic moiety selected from the group consisting of alkylidene, cycloalkylidene, arylidene, alkarylidene, and aralkylidene, with the total number of carbon atoms in $R^{12}+R^{13}$ being at least 5 and less than about 30 and which may contain one or more heteratoms selected from the group consisting of O, N and S and functional groups selected from the group consisting of OH, $CO_2$, ethers, amines, amides and carbon-to-carbon double bonds;
$R^3$ represents a divalent organic radical having a carbon directly attached to a silicon;
$R^4$ represents radicals selected from the group consisting of H and a lower alkyl;

A represents a radical selected from the group consisting of $CO_2$ and $SO_3$;

Z represents a radical selected from the group consisting of $NR^6R^7R^8R^9$ and an alkali metal, wherein $R^6$ represents H or a lower alkyl and $R^7$, $R^8$ and $R^9$ independently represent radicals selected from the group consisting of H and a lower alkyl, with the formula weight of $R^7+R^8+R^9$ being less than about 300;

X represents a halide or the radical $OR^{10}$, wherein $R^{10}$ represents H, a lower alkyl, aryl or alkaryl radicals or

wherein $R^{11}$ represents a lower alkyl;

$n_2$ is the integer 1 to 3;

$n_4$ is the integer 1;

a is the integer 0 or 1; and b is the integer 1.

14. The silanes of claim 12 wherein at least one of $R^{12}$ and $R^{13}$ contain at least one heteroatom selected from the group consisting of O, N and S and at least one functional group selected from the group consisting of OH, $CO_2$, ethers, amines, amides and carbon-to-carbon double bonds.

15. The silanes of claim 13 wherein X is $OR^{10}$.

16. The silanes wherein said silanes are defined by the following structural formula:

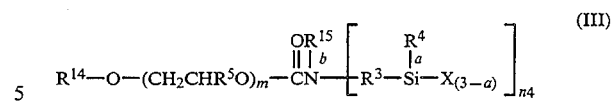

wherein $R^{14}$ represents a hydrophobic monovalent aryl, alkaryl or aralkyl organic radicals and may contain one or more heteratoms selected from the group consisting of O, N and S and functional groups selected from the group consisting of OH, $CO_2$, ethers, amines, amides and carbon-to-carbon double bonds;

$R^5$ represents H or a lower alkyl;

$R^{15}$ represents H or a lower alkyl;

$R^3$ represents a divalent organic radical having a carbon directly attached to silicon;

$R^4$ represents radicals selected from the group consisting of H and a lower alkyl;

X represents a halide, or the radical $OR^{10}$, wherein $R^{10}$ represents H, a lower alkyl, aryl or alkaryl organic radicals or

wherein $R^{11}$ represents a lower alkyl;

m is an integer ranging from 5 to about 70;

a is the integer 0 or 1;

b is the integer 1; and $n_4$ is the integer 1.

17. The silanes of claim 16 wherein $R^{14}$ contains a functional group selected from the group consisting of ether amide and ester.

18. The silanes of claim 16 wherein X is $OR^{10}$.

* * * * *